(12) United States Patent
Berd

(10) Patent No.: US 6,403,104 B1
(45) Date of Patent: Jun. 11, 2002

(54) HAPTEN-CONJUGATED MAMMALIAN CELLS AND METHODS OF MAKING AND USING THEREOF

(75) Inventor: David Berd, Wyncote, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/526,395

(22) Filed: Mar. 16, 2000

Related U.S. Application Data

(60) Provisional application No. 60/124,672, filed on Mar. 16, 1999.

(51) Int. Cl.$^7$ .............................................. A61K 39/00
(52) U.S. Cl. .................. 424/277.1; 424/93.1; 424/93.7
(58) Field of Search ............................. 424/277.1, 93.7, 424/93.1

(56) References Cited

U.S. PATENT DOCUMENTS 5,290,557 A    3/1994   Mason et al.

FOREIGN PATENT DOCUMENTS

| WO | WO 96/40173 | 12/1996 |
| WO | WO 98/14206 | 4/1998 |
| WO | WO 99/52546 | 10/1999 |

OTHER PUBLICATIONS

Sato, T. et al. Dinotrophenyl–modified autologous melanoma vaccine induces a T cell response to hapent–modified, melanoma peptides. Clinical Immunology and Immunopathology, 85:265–272, 1997.*
Berd et al., Proc. Of ASCO, 1983; 2:56, abs. C–217.
Sensi, M. et al., Proceedings of AACR, 1996; 37:473, Abstract #3229.
Russo, V., et al., Int. J. Cancer, 1996; 67:457–460.
Parmiani, G. et al., Cancer Res. Ins., 1996; S12–S13.
Berd D, et al., Annual Meeting Abstracts: 1997 Annual Meeting of ASCO, 438.
Berd, D. et al., Proceeding of ASCO: Immunobiology & Biologic Therapy, 1998; 17:434a.
Berd, D. et al., Proc. Am. Assoc. Cancer Res., 1998; 39:356, Abstract #2431.
Dunton, C. et al., Proc. Soc. Gyn. Oncol., Feb. 9, 1998, Orlando Fl.
Hammerberg, C., et al., The Journal of Immunology; 153(11):4915–4924, 1994.

* cited by examiner

*Primary Examiner*—Sheela Huff
(74) *Attorney, Agent, or Firm*—Darby & Darby

(57) ABSTRACT

The present invention is directed to mammalian cells conjugated to a hapten and methods of making and using thereof. Conjugating hapten to mammalian cells is a useful way of preventing cells from growing and may be used in the place of any conventional treatment, for example, irradiation. Thus, the invention relates to mammalian cells in general, for example human cells, which cells are in substantially no growth phase and a method of placing the cells in a substantially no growth phase by conjugating them to a hapten. The invention is further directed to compositions containing hapten-modified tumor cells and extracts and methods of treating cancer by administering a therapeutically effective amount of a composition containing a tumor cell or tumor cell extract to a subject in need of such treatment. The tumor cells and extracts of the invention and compositions thereof are capable of eliciting T lymphocytes that have a property of infiltrating a mammalian tumor, eliciting an inflammatory immune response to a mammalian tumor, eliciting a delayed-type hypersensitivity response to a mammalian tumor and/or stimulating T lymphocytes in vitro. The invention also relates to an effective vaccination schedule useful for inducing an antitumor response in a mammalian patient suffering from cancer by inducing at least one of the following: tumor necrosis, tumor regression, tumor inflammation, tumor infiltration by activated T lymphocytes, delayed-type hypersensitivity response, and prolongation of patient survival. Furthermore, the invention relates to an improved, simplified and economical method for preparing the hapten-conjugated tumor cells for administration as a vaccine by eliminating a separate step of treating cells (by irradiation, for example) to place them in a no growth phase.

32 Claims, No Drawings

HAPTEN-CONJUGATED MAMMALIAN CELLS AND METHODS OF MAKING AND USING THEREOF

This patent application claims the priority of U.S. provisional patent application No. 60/124,672, filed Mar. 16, 1999 which is incorporated herein by reference.

FIELD OF THE INVENTION

The present invention is directed to mammalian cells conjugated to a hapten, and methods of making and using thereof. Conjugating hapten to mammalian cells is an alternative strategy to prevent cells from proliferating, which may be used instead of conventional irradiation treatment. Compositions comprising hapten-modified tumor cells and tumor cell extracts, and methods of treating cancer by administering a therapeutically effective amount of a composition comprising a tumor cell or tumor cell extract to a subject in need of such treatment, are also within the scope of the invention. The invention also provides an effective vaccination schedule useful for inducing an antitumor response in a patient suffering from cancer.

BACKGROUND OF THE INVENTION

Preventing Growth of Mammalian Cells

In various in vitro and in vivo procedures using mammalian cells, there is a need to prevent the mammalian cells from growing and dividing, i.e., proliferating. Traditionally, irradiation of mammalian cells has been used for this purpose. For example, mammalian tumor cells were irradiated prior to administration as a vaccine to a melanoma patient (Berd et al., Cancer Res., 1986; 46:2572–77). Similarly, McCune et al. (Cancer, 1981; 47:1984–87) describe irradiation of renal carcinoma cells for purposes of therapy. However, there remains a need in the art for strategies to prevent cell proliferation which does not involve cell irradiation.

Hapten-conjugated Tumor Cell Vaccines

An autologous whole-cell vaccine modified with the hapten dinitrophenyl (DNP) has been shown to produce inflammatory responses in metastatic sites of melanoma patients. Post-surgical adjuvant therapy with DNP-modified vaccine produces survival rates that are markedly higher than those reported for surgery alone. Intact or viable cells are preferred for the vaccine.

U.S. Pat. No. 5,290,551, to David Berd, discloses and claims vaccine compositions comprising haptenized melanoma cells. Melanoma patients who were treated with these cells developed a strong immune response. This response could be detected in a delayed-type hypersensitivity (DTH) response to haptenized and non-haptenized tumor cells. More importantly, the immune response resulted in increased survival rates of melanoma patients.

Haptenized tumor cell vaccines have also been described for other types of cancers, including lung cancer, breast cancer, colon cancer, pancreatic cancer, ovarian cancer, and leukemia (see U.S. patent application Ser. No. 08/203,004, filed Feb. 28, 1994; International Patent Application No. PCT/US96/09511; U.S. patent application Ser. No. 08/899,905, filed Jul. 24, 1997).

Although the above studies describe successful immunotherapy methods using hapten-conjugated tumor cells, there remains a need in the cancer treatment art for additional and improved methods for inducing an anti-tumor response and improved hapten-modified tumor-cell. Applicant has now surprisingly discovered a simplified method for preparing hapten-modified tumor cell which eliminates the need for irradiation, thereby offering procedural and financial advantages in the production of hapten-modified tumor-cell vaccines.

SUMMARY OF THE INVENTION

The present invention relates to mammalian cells in a substantially non-proliferative state compositions containing hapten-modified tumor cells and methods for inducing an antitumor response in a patient suffering from cancer by administering the compositions of the invention.

In one embodiment, the invention relates to a mammalian cell, including a tumor cell, in a substantially non-prolierative state.

In another embodiment, the present invention relates to a method for placing a mammalian cell in a substantially non-proliferative state, which does not comprise irradiating the cell.

In yet another embodiment, the present invention is directed to a composition comprising a hapten modified mammalian tumor cell substantially in a non-proliferative state.

In still another embodiment, the invention provides for a vaccine composition comprising a therapeutically effective amount of a hapten-modified mammalian, preferably human, tumor cell which is substantially in a non-proliferative state.

In another aspect, the present invention is directed to a method of treating cancer comprising administering to a mammal, preferably a human, a composition comprising a therapeutically effective amount of a hapten modified human tumor cell, which has not been exposed to irradiation, wherein said mammal suffers from a malignant tumor of the same type as said tumor cell membrane.

In a further aspect, the invention is directed to a method of treating cancer according to weekly vaccinations using the non-proliferative hapten-modified tumor cell compositions described herein.

In yet another aspect, the invention relates to a simplified method for making the non-proliferative hapten-modified tumor cell compositions of the invention.

DETAILED DESCRIPTION OF THE INVENTION

The present invention is directed to mammalian cells conjugated to a hapten and methods of making and using thereof. Conjugating hapten to mammalian cells is an alternative strategy for preventing cells from growth, i.e., multiplication and may be used instead of a conventional irradiation treatment. Thus, the invention relates generally to mammalian cells, for example human cells, which are substantially in a non-proliferative state and a method of placing the cells in such a state by conjugating them to a hapten. Further, the compositions and methods described in the following PCT applications can advantageously be modified according to the present invention: PCT/US96/09511 (WO 96/40173), PCT/US97/15741 (WO 98/14206), PCT/US98/20888, PCT/US98/16660, PCT/US99/27442, PCT/US99/07725 (WO 99/52546), and PCT/US99/31297.

The present invention is also directed to cancer immunotherapy. A tumor composition and methods of treating cancer are included in the scope of the invention. The invention further relates to a method of inducing an antitumor response according to a weekly vaccinations with non-proliferative hapten-conjugated tumor cell compositions produced by the simplified method of the invention.

For purposes of the present invention an antitumor response is at least one of the following: tumor necrosis, tumor regression, tumor inflammation, tumor infiltration by activated T lymphocytes, delayed-type hypersensitivity response, and prolongation of patient survival. The tumor cells and extracts of the invention and compositions thereof are capable of eliciting T lymphocytes that have a property of infiltrating a mammalian tumor, eliciting an inflammatory immune response to a mammalian tumor, eliciting a delayed-type hypersensitivity response to a mammalian tumor and/or stimulating T lymphocytes in vitro.

An anti-tumor response resulting from the treatment according to the present invention may be a partial or a complete regression of the metastatic tumor or a stable disease. A "complete" regression indicates about 100% regression for a period of at least one month, more preferably for a period of at least three months. A "partial" regression indicates more than about 50% regression for a period of at least one month, more preferably for a period of at least three months. A "stable" disease indicates a condition in which there is no significant growth of the tumor after the vaccine treatment. Another anti-tumor response that may be observed following the treatment of the invention is prolongation of survival.

Any malignant tumor may be treated according to the present invention including metastatic and primary cancers and solid and non-solid tumors. Solid tumor include carcinomas, and non-solid tumors include hematologic malignancies. Carcinomas include and are not limited to adenocarcinomas and epithelial carcinomas. Hematologic malignancies include leukemias, lymphomas, and multiple myelomas. The following are non-limiting examples of the cancers treatable with isolated modified tumor cell membranes according to the methods of the present invention: ovarian, including advanced ovarian, leukemia, including and not limited to acute myelogenous leukemia, colon, including colon metastasized to liver, rectal, colorectal, melanoma, breast, lung, kidney, and prostate cancers. The ovarian cancers may be adenocarcinomas or epithelial carcinomas. Colon and prostate cancers are adenocarcinomas. Leukemias may originate from myeloid bone marrow or lymph nodes. Leukemias may be acute, exhibited by maturation arrest at a primitive stage of development, and chronic, exhibited by excess accrual of mature lymphoid or myeloid cells. Stage I, II, III, or IV cancer may be treated according to the present invention, preferably stages III and IV, even more preferably stage III. Any mammal, preferably a human, may be treated according to the present invention.

The compositions of the present invention are prepared from a tumor cell or tumor cell extract. A tumor cell may be a malignant or pre-malignant cell of any type of cancer. In accordance with the present invention, pre-malignant refers to any abnormal cell suggestive of a cancer cell, which is not yet a cancer cell; such as and not limited to dysplastic changes in cervical cells which ultimately lead to cervical cancer, and dysplastic nevi which are abnormal skin cells which lead to melanoma.

The tumor cells and extracts preferably originate from the type of cancer which is to be treated. For example, a melanoma cell or cell extract is used to treat melanoma type cancer. The tumor cells and extracts may be, and are not limited to, autologous and allogenic cells dissociated from biopsy specimens or tissue culture, as well as stem cells and extracts from these sources. In one preferred embodiment, the cells and extracts are autologous. However, any non-allogeneic cell, including tumor cells produced in culture from autologous cells isolated from the patient's tumor, may be used. Tumor cells need not be completely (i.e., 100%) genetically identical to either the tumor cell or the non-tumor, somatic cell of the treated patient. Genetic identity of the MHC molecules between the tumor cell and the patient is generally sufficient. Additionally, there may be genetic identity between a particular antigen on the melanoma cell and an antigen present on the patient's tumor cells. Genetic identity may be determined according to the methods known in the art. For purposes of the present invention, a tumor cell that has been genetically altered (using for example recombinant DNA technology) to become genetically identical with respect to, for example, the particular MHC molecules of the patient and/or the particular antigen on the patient's cancer cells is within the meaning of "non-allogeneic" and within the scope of the present invention. Such cells may also be referred to as "MHC-identical" or "MHC-compatible."

T cells are lymphocytes which mediate two types of immunologic functions, effector and regulatory, secrete proteins (lymphokines), and kill other cells (cytotoxicity). Effector functions include reactivity such as delayed hypersensitivity, allograft rejection, tumor immunity, and graft-versus-host reactivity. Lymphokine production and cytotoxicity are demonstrated by T cell effector functions. Regulatory functions of T cells are represented by their ability to amplify cell-mediated cytotoxicity by other T cells and immunoglobulin production by B cells. The regulatory functions also require production of lymphokines. T cells produce gamma interferon (IFNγ) in response to an inducing stimulus including and not limited to mitogens, antigens, or lectins.

Proliferation of T cells may be observed by uptake by T cells of modified nucleic acids, such as and not limited to $^3$H thymidine, $^{125}$IUDR (iododeoxyuridine); and dyes such as 3-(4,5-dimethylthiazol-2-yl)-2,5-diphenyltetrazolium bromide (MTT) which stains live cells. In addition, production of cytokines such as and not limited to IFNγ, tumor necrosis factor (TNF), and IL-2. Production of cytokines is preferably in an amount of greater than 15 picograms/ml, more preferably about 20 to about 30 picograms/ml, even more preferably about 50 picograms/ml.

The tumor cells of the present invention may be live cells. In accordance with the invention, the tumor cells are incapable of growing in the body of the patient after injection as a consequence only of haptenization, e.g., with DNP. In other words, the cells are "substantially in a no growth phase."

Other methods of preventing cells from growing are known to those of skill in the art, for example, tumor cells may be irradiated prior to use. In one embodiment, tumor cells or extracts are irradiated at about 2500 cGy to prevent the cells from growing after injection. The surprising advantage of the invention is that the invention cells are not irradiated or otherwise separately treated to prevent their growth in the body of a human because haptenization alone prevents growth of the tumor cells after injection as shown in Example 1. For purposes of the present invention, the phrase "separately treated to render tumor cells (or mammalian cells in general) incapable of growing in the body of a patient" means that the only means for rendering the cells incapable of growing in a human is by hapten conjugation, and no other methods (such as irradiation for example) are used in addition to haptenization for this purpose.

In one embodiment of the invention, any mammalian cell is conjugated to a hapten to place it in a substantially no growth phase. Preferably, the cells are not separately treated (i.e., in addition to haptenization) to render them incapable of growing. Such mammalian cells are useful, for example, in any procedure, treatment or assay known to persons of skill in the art in which irradiated cells are traditionally used.

The compositions of the invention may be employed in the method of the invention singly or in combination with other compounds, including and not limited to other compositions of the invention. For purposes of the present invention, coadministration includes administration together and consecutively. The cancer cells may be co-administered with other compounds including and not limited to cytokines such as interleukin2, interleukin-4, gamma interferon, interleukin-12, and GM-CSF. The tumor cells of the invention may also be used in conjunction with other cancer treatments including and not limited to chemotherapy, radiation, antibodies, oligonucleotide sequences, and anti-sense oligonucleotide sequences.

The compositions of the invention may be administered in a mixture with a pharmaceutically-acceptable carrier, selected with regard to the intended route of administration and the standard pharmaceutical practice. Dosages may be set with regard to weight, and clinical condition of the patient. The proportional ratio of active ingredient to carrier naturally depend on the chemical nature, solubility, and stability of the compositions, as well as the dosage contemplated. Amounts of the tumor cells and extracts of the invention to be used depend on such factors as the affinity of the compound for cancerous cells, the amount of cancerous cells present and the solubility of the composition. The composition of the present invention may be mixed with an immunological adjuvant and/or a pharmaceutically acceptable carrier. Any known aqueous vehicle useful in drug delivery, such as and not limited to saline, may be used in accordance with the present invention as a carrier. In addition, any adjuvant known to skilled artisans may be useful in the delivery of the present invention. The adjuvant has the property of augmenting an immune response to the tumor cell preparations of the present invention. Representative examples of adjuvants are BCG, or the synthetic adjuvant, QS-21 comprising a homogeneous saponin purified from the bark of *Quillaja saponaria*, *Corynebacterium parvum* (McCune et al., Cancer, 1979; 43:1619), saponins in general, detoxified endotoxin and cytokines such as interleukin-2, interleukin-4, gamma interferon (IFN-γ), interleukin-12, interleukin-15, GM-CSF and any combinations thereof.

Alternatively, the tumor cells may be added to antigen presenting cells. The tumor cell may be used to treat cancer together with another cell type, an antigen presenting cell, selected from the group consisting of autologous cultured macrophages and autologous cultured dendritic cells. Macrophages are any large ameboid mononuclear cell, regardless of origin, such as and not limited to histiocytes and monocytes, which phagocytose, i.e. engulf and destroy, other cells, dead tissue, degenerated cells, and the like. Macrophages are antigen presenting cells, which present antigens, including tumor antigens, to cells including T cells. Dendritic cells are also antigen presenting cells and appear to be closely related to macrophages, however, dendritic cells are more efficient antigen presenting cells than macrophages. They are potent stimulators of T cells and may be isolated from a variety of body organs and tissues including and not limited to blood, skin (where dendritic cells are referred to as Langerhans cells), and lymphoid tissues.

The antigen presenting cells with peptide or membrane bound thereto, for example, may be used to immunize patients. The patient's blood is obtained and macrophages or dendritic cells are extracted therefrom. High concentrations of the peptide (about 1 ng/ml to about 1 µg/ml, preferably about 10 ng/ml to about 100 ng/ml), or membrane (about $10^5$ to about $10^7$ cell equivalents (c.e.), cell equivalents are in relation to the number of starting cells, i.e., the amount of cell extract obtained from the indicated number of cells) are incubated with the cells overnight or for about 8 hours. When incubating with membranes, the membranes are phagocytized by the macrophages or dendritic cells. The macrophages or dendritic cells which have phagocytized the membranes are then used to immunize the patient (Grabbe, S., et al., Immunology Today 1995; 16:117–121).

The vaccine composition of the invention may contain, for example, at least $10^4$ tumor cells per dose, preferably at least $10^5$ cells, and most preferably at least $10^6$ cells. A dose is that amount of the vaccine composition that is administered in a single administration. In one embodiment, the vaccine composition contains from about $10^5$ to about $2.5 \times 10^7$ cells. extract per dose, more preferably about $5 \times 10^6$ cells. In one preferred embodiment, the vaccine composition contains a maximum of $7.5 \times 10^6$ cells extract. The amount of the tumor cells of the invention to be used generally depends on such factors as the affinity of the compound for tumor cells, the amount of tumor cells, and the solubility of the composition. Dosages may be set, e.g., with regard to weight and clinical condition of the patient.

The vaccine composition of the invention may be packaged in a dosage form suitable for intradermal, intravenous, intraperitoneal, intramuscular, and subcutaneous administration. Alternatively, the dosage form may contain the preparations of the invention (e.g. tumor cells) to be reconstituted at the time of the administration with, for example, a suitable diluent.

The tumor cells and compositions thereof may be administered by any suitable route, including inoculation and injection, for example, intradermal, intravenous, intraperitoneal, intramuscular, and subcutaneous. There may be multiple sites of administration per each vaccine treatment. For example, the vaccine composition may be administered by intradermal injection into at least two, and preferably three, contiguous sites per administration. In one embodiment of the invention, the vaccine composition is administered on the upper arms or legs.

Prior to administration of the vaccine composition of the invention, the subject may be immunized to the hapten which is to be used to modify tumor cells and membranes by applying it to the skin. For example, dinitrofluorobenzene (DNFB) may be used. In one embodiment of the invention, the patient is not immunized to a hapten prior to vaccine administration. Subsequently (about two weeks later, for example), the subject may be injected with a tumor cell or extract composition. The composition may be administered (such as by reinjection) for a total of at least three and preferably at least six treatments. In one embodiment, the total number of administrations (including the initial administration) may be eight, and in another embodiment may be ten. The vaccination schedule may be designed by the attending physician to suit the particular subject's condition. The vaccine injections may be administered, for example, every 4 weeks, preferably every 2 weeks, and most preferably every week. In one preferred embodiment, the vaccine is injected every week for a total of six treatments. Haptenized and non-haptenized vaccine may be alternated. In one preferred embodiment, all vaccines contain hapten modified tumor cells. A booster vaccine may be administered. Preferably, one or two booster vaccines are administered. The booster vaccine may be administered, for example, after about six months or about one year after the initial administration.

The drug cyclophosphamide (CY) may be administered several days (e.g. 3 days) prior to each vaccine administration to augment the immune response to the tumor cells. In one preferred embodiment, CY is administered only prior to the first vaccine injection.

The haptenized, or chemically-linked, form of the vaccine may include a tumor cell haptenized to dinitrophenyl (DNP) for example. Other haptens include and are not limited to trinitrophenyl, N-iodoacetyl-N'-(5-sulfonic 1-naphthyl) ethylene diamine, trinitrobenzenesulfonic acid, fluorescein isothiocyanate, arsenic acid benzene isothiocyanate, trinitrobenzenesulfonic acid, sulfanilic acid, arsanilic acid, dinitrobenzene-S-mustard. Combinations of hapten may also be used.

Haptens generally include a reactive group for conjugation to a substituent on an amino acid side chain of a protein or polypeptide (e.g., a free carboxylic acid group as in the case of aspartic acid or glutamic acid; the $\bar{y}$-amino group of lysine; the thiol moiety of cysteine; the hydroxyl group of serine or tyrosine; the imidazole moiety of histidine; or the aryl groups of tryptophan, tyrosine, or phenylalanine). As used herein, the term "reactive group" refers to a functional group on the hapten that reacts with a functional group on a peptide or protein. The term "functional group" retains its standard meaning in organic chemistry. These reactive groups on a hapten are termed herein the "hapten reactive group". Numerous hapten reactive groups are known, which interact with the substituents present on the side chains of amino acids that comprise peptides and proteins. Preferred examples of such reactive groups for conjugation to specific polypeptide substituents are carboxylic acid or sulfonic acid derivatives (including acid chlorides, anhydrides, and reactive carboxylic esters such as N-hydroxysuccinimide esters), imidoesters, diazonium salts, isocyanates, isothiocyanates, halonitrobenzenes, α-halocarbonyl compounds, maleimides, sulfur mustards, nitrogen mustards, and aziridines.

Hapten reactive groups that would form a covalent bond with primary amines present on amino acid side chains would include, but not be limited to, acid chlorides, anhydrides, reactive esters, α,β-unsaturated ketones, imidoesters, and halonitrobenzenes. Various reactive esters with the capability of reacting with nucleophilic groups such as primary amines are available commercially, e.g., from Pierce (Rockford, Ill.).

Carboxylic acids in the presence of carbodiimides, such as EDC, can be activated, allowing for interaction with various nucleophiles including primary and secondary amines. Alkylation of carboxylic acids to form stable esters can be achieved by interaction with sulfur or nitrogen mustards or haptens containing either an alkyl or aryl aziridine moiety.

Interaction of the aromatic moieties associated with certain amino acids can be accomplished by photoactivation of aryl diazonium compound in the presence of the protein or peptide. Thus, modification of the aryl side chains of histidine, tryptophan, tyrosine, and phenylalanine, particularly histidine and tryptophan, can be achieved by the use of such a reactive functionality.

Functional groups reactive with sulfhydryl groups. There are several reactive groups that can be used to modify sulfhydryl groups present on the side chains of amino acids. Haptens containing an α,β-unsaturated ketone or ester moiety, such as maleimide, provide a reactive functionality that can interact with sulfhydryl as well as amino groups. In addition, a reactive disulfide group, such as 2-pyridyldithio group or a 5,5'-dithio-bis-(2-nitrobenzoic acid) group, can react as well. Some examples of reagents containing reactive disulfide bonds include N-succinimidyl 3-(2-pyridyl-dithio) propionate (Carlsson, et al., Biochem J., 173:723–737, 1978), sodium S-4-succinimidyloxycarbonyl-alpha-methylbenzylthiosulfate, and 4-succinimidyloxycarbonyl-alpha-methyl-(2-pyridyldithio)toluene. Some examples of reagents comprising reactive groups having a double bond that reacts with a thiol group include succinimidyl 4-(N-maleimidomethyl)cyclohexahe-1-carboxylate and succinimidyl m-maleimidobenzoate.

Other functional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. Many of the above-mentioned reagents and their sulfonate salts are available from Pierce.

Haptens also include a hapten recognition group that interacts with antibody. The recognition group is irreversibly associated with the hapten reactive group. Thus, when the hapten reactive group is conjugated to a functional group on the target molecule, the hapten recognition group is available for binding with antibody. By selecting an appropriate hapten reactive group, antibody recognition of and binding to a hapten recognition group can be made independent of the functional group to which the hapten is conjugated. When this is the case, the haptens are functionally equivalent, and are said to share antibody binding features. This is the case even though chemically the haptens differ, to provide for conjugation to different functional groups.

Examples of different hapten recognition groups include without limitation to dinitiophenyl, trinitrophenyl, fluorescein, other aromatics, phosphorylcholine, peptides, advanced glycosylation endproducts (AGE), carbohydrates, etc.

In a specific embodiment, the same hapten recognition group can be coupled to different amino acids through different hapten reactive groups. For example, the reagents dinitrobenzene sulfonic acid, dinitro-phenyldiazonium, and dinitrobenzene-S-mustard, all form the dinitrophenyl hapten coupled to amino groups, aromatic groups, and carboxylic acid groups, respectively. Similarly, an arsenic acid hapten can be coupled by reacting arsenic acid benzene isothiocyanate to amino groups or azobenzenearsenate to aromatic groups.

In one embodiment of the present invention, a method of treating a patient suspected of having cancer, may comprise administering a pharmaceutically acceptable amount of cyclophosphamide, and a pharmaceutically acceptable amount of a composition comprising live tumor cells or tumor cells substantially in a non-metabolic state or a mixture thereof. The composition may be mixed with an immunological adjuvant and/or a pharmaceutically acceptable carrier. The haptenized vaccine may optionally be followed by administration of a pharmaceutically acceptable amount of a non-haptenized vaccine.

In another embodiment of the invention, the composition of the invention is administered every week for a period of at least three weeks, preferably at least six weeks, and the first administration is preceded by a pharmaceutically acceptable amount of cyclophosphamide. Preferably, the composition may contain a maximum of about $7.5 \times 10^6$ cells. The patient need not be immunized to hapten prior to vaccine administration.

The tumor cells for use in the present invention may be prepared as follows. Tumor masses are processed as described by Berd et al. (1986), supra. The cells are extracted by enzymatic dissociation with collagenase and DNAse by mechanical dissociation, frozen in a controlled rate freezer, and stored in liquid nitrogen until needed. On the day that a patient is to be skin tested or treated, the cells are thawed and washed. They are washed again and then suspended in Hanks balanced salt solution without phenol red. Conjugation of the prepared cells with DNP is preferably performed by the method of Miller and Claman (J. Immunol., 1976; 117, 1519).

The following procedure may be used for tumor cell haptenization. About 100 mg of DNFB (Sigma Chemical Co., St. Louis, Mo.) is dissolved in about 0.5 ml of 70% ethanol. About 99.5 ml of PBS is added. DNFB concentration should be about 152 mg/0.1 ml. The solution is stirred overnight in a 37° C. water bath. The shelf life of the solution is about 4 weeks. The cells are thawed and the pellet resuspended in $5 \times 10^6$ cells/ml in Hanks balanced salt solution. About 0.1 ml DNFB solution is added to each ml of cells and incubated for about 30 minutes at room temperature. Similarly, other haptens such as and not limited to trinitrophenyl, N-iodoacetyl-N'-(5-sulfonic 1-naphthyl) ethylene diamine, trinitrobenzenesulfonic acid, fluorescein isothiocyanate, arsenic acid benzene isothiocyanate, trinitrobenzenesulfonic acid, sulfanilic acid, arsanilic acid, dinitrobenzene-S-mustard and combinations thereof may be used. The cells are then washed twice in Hanks balanced salt solution. Cells are suspended in about five volumes of about 30 mM sodium bicarbonate buffer with about 1 mM phenyl methyl sulfonyl fluoride and disrupted with a glass homogenizer. Residual intact cells and nuclei are removed by centrifugation at about 1000 g. The membranes are pelleted by centrifugation at 100,000 g for 90 minutes. The membranes are resuspended in about 8% sucrose and frozen at about −80° C. until needed.

Numerous human cancer vaccines have been developed and studied. Although these conventional vaccines sometimes induce weak immunity to a patient's cancer, tumor regression has rarely been observed. The development of inflammatory responses in metastatic tumors was surprisingly found with the DNP-vaccine of the present invention. Tumor became reddened, warm and tender. Ultimately, in some cases, the tumor regressed to the extent that it disappeard, to the naked eye and microscopically. Microscopically, infiltration of T lymphocytes into the tumor mass was observed. Therefore, this approach, which increases the inflammatory response and the number and capacity of lymphocytes entering the tumor, is a significant advance in the art.

The effectiveness of the vaccine may be improved by adding various biological response modifiers. These agents work by directly or indirectly stimulating the immune response. Biological response modifiers of the present invention include and are not limited to interleukin-12 and gamma interferon. In this embodiment, IL12 will be given following the each vaccine injection. Administration of IL12 to patients with inflammatory responses is believed to cause the T lymphocytes within the tumor mass to proliferate and become more active. The increased T cell numbers and functional capacity leads to immunological destruction of the tumors. Dosages for IL12 are prepared in accordance with the dosage indications set forth above.

Patients with metastatic melanoma can be treated using an immunotherapy regimen with the following components: 1) vaccine consisting of autologous tumor cells conjugated to DNP; and 2) low dose cyclophosphamide pretreatment. Patients are evaluated to determine whether tumor regression occurs, to monitor tumor inflammatory responses, and to measure delayed type hypersensitivity response to autologous melanoma cells, DNFB (the form of DNP used for skin sensitization), DNP-conjugated autologous lymphocytes, diluent (Hanks solution), purified protein derivative (PPD), and recall antigens (candida, trichophyton, and mumps). Patients who are considered to be deriving benefit (clinical or immunological) from the therapy are continued in the immunotherapy regimen. Subsequent vaccines may be given without cyclophosphamide. In a similar experiment, Interleukin 2 linked to polyethylene glycol has been found to not be effective.

In another embodiment, a vaccine comprising cancer cells conjugated to a hapten and mixed with an immunological adjuvant, such as Bacillus Calmette-Guerin, BCG, is used.

In the present invention, biopsies from human melanoma metastases are examined for expression of cytokine mRNA using RT-PCR. mRNA for IFNγ is found in post-DNPvaccine, inflamed metastases, but only rarely in pretreatment metastases, even those containing large numbers of residual lymph node lymphocytes. Moreover, the Type II cytokine, IL10, is found in almost all melanoma metastases and appears to be produced by the melanoma cells themselves.

Patients with metastatic melanoma treated with an autologous, DNP-modified vaccine develop inflammatory responses at tumor sites. Histologically, these inflamed lesions are characterized by T cell infiltration which is sometimes associated with tumor cell destruction. In the present invention, biopsy specimens of 8 subcutaneous metastases that had developed inflammation following vaccine treatment were tested for expression of mRNA for IFNγ, IL4, TNF, and IL10. Post-vaccine, inflamed biopsies contained mRNA for IFNγ (5/8), IL4 (4/8) or both (3/8), and for TNF (4/7). In contrast, IFNγ mRNA was detected in only 1/17 and TNF mRNA in 2/16 control specimens (pretreatment lymph node metastases or non-inflamed subcutaneous metastases). mRNA for IL10, a cytokine with anti-inflammatory properties, was detected in 24/25 melanoma metastases and was independent of lymphoid content; in situ PCR confirmed that melanoma cells were the major source. These findings provide a new parameter by which to measure the effects of cancer immunotherapy.

The present invention is aimed at analyzing freshly obtained metastatic melanoma biopsies for the presence of cytokine mRNA which correlates with a productive immune response at the tumor site. The expression of IFNγ or IL4 mRNA is characteristic of melanoma metastases that have developed an inflammatory response following administration of DNP-modified autologous vaccine on the other hand, expression of IL10 mRNA is independent of an inflammatory response and seen in nearly all melanoma biopsy specimens. Examination of cell lines derived from melanoma biopsies as well as in situ PCR analysis demonstrated that the source of IL10 is melanoma cells themselves rather than the associated lymphocytes.

The scope of the present invention also includes a method of screening for cytokine production by a tumor to determine the efficacy of an autologous, irradiated hapten conjugated cell composition in a patient suspected of having cancer, said method comprising administering said hapten conjugated composition to said patient; obtaining a sample comprising nucleic acids from a patient tissue sample; amplifying nucleic acids specific for a cytokine or amplifying a signal generated by hybridization of a probe specific to a cytokine specific nucleic acid in said tissue sample; and detecting the presence of the amplified nucleic acids or the amplified signal wherein the presence of amplified nucleic acids or amplified signal indicates cancer, wherein the presence of amplified nucleic acids or amplified signal from said patient tissue sample indicates efficacy of said hapten conjugated composition.

The tissue sample may be a malignant or premalignant tumor, for example, a melanoma tumor, or a subcutaneous inflammatory metastatic melanoma, for example. In addition, a tissue sample may be a solid or liquid tissue sample such as and not limited to all or part of a tumor, saliva, sputum, mucus, bone marrow, serum, blood, urine, lymph, or a tear from a patient suspected of having cancer.

Nucleic acids, such as DNA (including cDNA) and RNA (including mRNA), are obtained from the patient tissue sample. Preferably RNA is obtained from a tissue sample. Total RNA is extracted by any method known in the art such as described in Sambrook et al., *Molecular Cloning: A Laboratory Manual* (Cold Spring Harbor Laboratory, Cold Spring Harbor, N.Y., 1989), incorporated.

Nucleic acid extraction is followed by amplification of the same by any technique known in the art. The amplification step incudes the use of at least one primer sequence which is complementary to a portion of a cytokine specific sequence. Cytokine specific sequences are defined for purposes of the present invention to include (and are not limited to) all or part of sequences which encode IFNγ, TNF, IL-2, IL-12, and IL-13. Generally, the primer sequence is about 21 nucleotides to about 33 nucleotides, preferably about 21 nucleotides, about 31 nucleotides, 32 nucleotides, and about 33 nucleotides in length.

Where a template dependent process of amplification uses a pair of primers, one primer of the pair may comprise oligonucleotides which are complementary to nucleic acid sequences which encode cytokine specific proteins.

Alternatively, each of the two oligonucleotides in the primer pair may be specific to a nucleic acid sequence which encodes a cytokine. The primers may be designed to be complementary to separate regions of a cytokine sequence for example. By separate regions is meant that a first primer is complementary to a 3' region of a cytokine sequence and a second primer is complementary to a 5' region of a cytokine sequence. Preferably, the primers are complementary to distinct, separate regions and are not complementary to each other.

Any primer pairs which transcribe nucleic acids toward each other and which are specific for cytokines may be used in accordance with the methods of the present invention.

Total extraction of RNA is preferably carried out. As used herein, the term "amplification" refers to template-dependent processes and vector-mediated propagation which result in an increase in the concentration of a specific nucleic acid molecule relative to its initial concentration, or in an increase in the concentration of a detectable signal. As used herein, the term template-dependent process is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, J. D. et al., In: Molecular Biology of the Gene, 4th Ed., W. A. Benjamin, Inc., Menlo Park, Calif. (1987)). Typically, vector mediated methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., Molecular Cloning (A Laboratory Manual), Cold Spring Harbor Laboratory, 1982.

A number of template dependent processes are available to amplify the target sequences of interest present in a sample. one of the best known amplification methods is the polymerase chain reaction (PCR) which is described in detail in U.S. Pat. Nos. 4,683,195, 4,683,202 and 4,800,159, and in Innis et al., *PCR Protocols,* Academic Press, Inc., San Diego Calif., 1990. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended,primers will dissociate from the target to form reaction products, excess primers will bind to the target and to the reaction products and the process is repeated. Preferably a reverse transcriptase PCR amplification procedure may be performed in order to quantify the amount of mRNA amplified. Polymerase chain reaction methodologies are well known in the art.

Another method for amplification is the ligase chain reaction (referred to as LCR), disclosed in EPA No. 320,308. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes an alternative method of amplification similar to LCR for binding probe pairs to a target sequence.

Qbeta Replicase, described in PCT Application No. PCT/US87/00880 may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio] triphosphates in one strand of a restriction site (Walker, G. T., et al., Proc. Natl. Acad, Sci. USA 1992, 89:392–396), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and involves annealing several probes throughout a region targeted for amplification, followed by a repair reaction in which only two of the four bases are present. The other two bases can be added as biotinylated derivatives for easy detection. A similar approach is used in SDA.

Cytokine specific sequences can also be detected using a cyclic probe reaction (CPR). In CPR, a probe having a 31 and 51 sequences of non-cytokine specific DNA and middle sequence of cytokine specific RNA is hybridized to DNA which is present in a sample. Upon hybridization, the reaction is treated with RNaseH, and the products of the probe identified as distinctive products generating a signal which are released after digestion. The original template is annealed to another cycling probe and the reaction is repeated. Thus, CPR involves amplifying a signal generated by hybridization of a probe to a cytokine specific nucleic acid.

Still other amplification methods described in GB Application No. 2 202 328, and in PCT Application No. PCT/US89/01025, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS) (Kwoh D., et al, Proc. Natl. Acad. Sci. USA, 1989, 86:1173, Gingeras T. R., et al., PCT Publication WO 88/10315) including nucleic acid sequence based amplification (NASBA) and 3SR. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has prostate specific sequences. Following polymerization, DNA/RNA hybrids are digested with RNase H while double stranded DNA molecules are heat denatured again. In either case the single stranded DNA is made fully double stranded by addition of second prostate specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate prostate cancer specific sequences.

European Patent Publication No. 329822, discloses a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT Application WO 89/06700, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., In: *PCR Protocols: A Guide to Methods and Applications* 1990, Academic Press, N.Y.) and "one-sided PCR11 (Ohara, O., et al., Proc. Natl. Acad. Sci. USA, 1989; 86:5673–5677).

Methods based on ligation of two (or more) oligonucleotides in the presence of nucleic acid having the sequence of the resulting "di-oligonucleotide", thereby amplifying the di-oligonucleotide (Wu, D. Y. et al., Genomics 1989; 4:560) may also be used in the amplification step of the present invention.

Following amplification, the presence or absence of the amplification product may be detected. The amplified product may be sequenced by any method known in the art, including and not limited to the Maxam and Gilbert method, see Sambrook, supra. The sequenced amplified product may then be compared to results obtained with tissue excised prior to vaccine treatment. Tissue samples obtained prior to vaccine treatment should be free of cytokine sequences, particularly IFNγ, TNF, IL2, IL12, and IL13. The nucleic acids may be fragmented into varying sizes of discrete fragments. For example, DNA fragments may be separated according to molecular weight by methods such as and not limited to electrophoresis through an agarose gel matrix. The gels are then analyzed by Southern hybridization. Briefly, DNA in the gel is transferred to a hybridization substrate or matrix such as and not limited to a nitrocellulose sheet and a nylon membrane. A labelled probe is applied to the matrix under selected hybridization conditions so as to hybridize with complementary DNA localized on the matrix. The probe may be of a length capable of forming a stable duplex. The probe may have a size range of about 200 to about 10,000 nucleotides in length, preferably about 200 nucleotides in length. Mismatches such as and not limited to sequences with similar hydrophobicity and hydrophilicity, will be known to those of skill in the art once armed with the present disclosure. Various labels for visualization or detection are known to those of skill in the art, such as and not limited to fluorescent staining, ethidium bromide staining for example, avidin/biotin, radioactive labeling such as $^{32}P$ labeling, and the like. Preferably, the product, such as the PCR product, may be run on an agarose gel and visualized using a stain such as ethidium bromide. See Sambrook et al., supra. The matrix may then be analyzed by autoradiography to locate particular fragments which hybridize to the probe.

A diagnostic kit for screening for the efficacy of an autologous, irradiated, hapten conjugated cell composition comprising in one or more containers, a pair of primers, wherein one of the primers within said pair is complementary to a cytokine specific sequence, and a means for visualizing amplified DNA; said kit useful for determining the efficacy of said composition.

The invention is further illustrated by means of the following actual example which is meant to be illustrations only and are not intended to limit the present invention to this specific embodiment.

EXAMPLE 1

Inhibition of Vaccine Tumor Cell Proliferation by Hapten-conjugation

Tumor cells were obtained from biopsy samples of thirteen melanoma and nine ovarian cancer patients. The cells were isolated from tumor masses as described in the present specification, and frozen until needed. Enzymatic dissociation of tumor cells was used. A cell line established using melanoma cells from a patient was also used in this study. Tumor cells from each patient were then divided into four groups: (i) control tumor cells; (ii) irradiated tumor cells; (iii) hapten-conjugated tumor cells; and (iv) irradiated, hapten-conjugated tumor cells. The cells from groups (ii) and (iv) were irradiated at 2500 cGy. The cells were conjugated to a hapten as described in the present specification. The cells were then grown at 37° C. in tissue culture medium (RPMI-1640 with either 10% fetal calf serum or pooled human serum) in microtiter wells for 2–14 days. The wells were then pulsed with $^{125}$IUDR for four hours, the pellets were collected by an automatic cell harvester, and 125I incorporation was measured using a gamma counter. The counts per minute for each well indicates the proliferative capacity of the cells. The results are represented in Table 1.

Referring to Table 1, cell growth was measured at different days to ensure that the cells did not recover from the anti-proliferative effects of irradiation or DNP, or both.

TABLE 1

INHIBITION OF VACCINE CELL PROLIFERATION BY IRRADIATION TREATMENT (RT) AND/OR HAPTENIZATION (DNP)

| Patient ID | Cell Type | Date of Expt. | Day of culture | (i) No Rx[1] | (ii) RT[2] | (iii) DNP[3] | (iv) RT + DNP[4] |
|---|---|---|---|---|---|---|---|
| JB | mel cell line | 10/8/98 | 4 | 24,292[5] | 1,784 | 204 | 625 |
| HB | MEL VACC | 10/26/98 | 4 | 88,682 | 6,490 | 348 | 139 |
| ND | MEL VACC | 10/1/98 | 3 | 1,270 | 1,055 | 699 | 667 |
| BE | MEL VACC | 12/8/98 | 2 | 49,442 | 18,264 | 540 | 555 |
| BE | MEL VACC | 12/8/98 | 7 | 274,336 | 7,574 | 540 | 401 |
| EM | MEL VACC | 11/3/98 | 6 | 14,482 | 1,901 | 883 | 692 |
| DM | MEL VACC | 12/8/98 | 2 | 45,767 | 6,083 | 294 | 475 |
| DM | MEL VACC | 12/8/98 | 7 | 101,085 | 17,085 | 377 | 428 |
| DM | MEL VACC | 12/8/98 | 10 | 114,416 | 13,098 | 145 | 302 |
| DM | MEL VACC | 12/8/98 | 14 | 94,474 | 9,555 | 203 | 267 |
| ER | MEL VACC | 12/8/98 | 2 | 6,946 | 637 | 261 | 421 |
| ER | MEL VACC | 12/8/98 | 7 | 14,655 | 305 | 179 | 378 |
| JS | MEL VACC | 12/8/98 | 2 | 5,078 | 1,614 | 405 | 862 |
| JS | MEL VACC | 12/11/98 | 7 | 22,955 | 3,960 | 184 | 463 |
| MC | OVAR VACC | 12/11/98 | 3 | 6,546 | 2,559 | 268 | 556 |
| MC | OVAR VACC | 12/11/98 | 7 | 10,836 | 1,919 | 226 | 279 |
| GK | OVAR VACC | 12/11/98 | 3 | 1,242 | 626 | 216 | 475 |
| GK | OVAR VACC | 12/11/98 | 7 | 4,515 | 809 | 254 | 290 |
| KM | OVAR VACC | 12/11/98 | 3 | 14,141 | 6,017 | 295 | 336 |
| KM | OVAR VACC | 12/11/98 | 7 | 37,824 | 8,889 | 227 | 408 |
| KM | OVAR VACC | 12/11/98 | 10 | 20,222 | 4,291 | 101 | 300 |
| SW | OVAR VACC | 12/11/98 | 3 | 3,686 | 1,518 | 174 | 334 |
| SW | OVAR VACC | 12/11/98 | 7 | 9,093 | 1,110 | 179 | 255 |

[1] No Rx - no irradiation treatment
[2] RT - irradiation treatment (2500 cGy)
[3] DNP - haptenization
[4] RT + DNP - haptenization and irradiation treatment (2500 cGy)
[5] Counts per minute (CPM)

The above results demonstrate that haptenization alone inhibits proliferation of tumor cells. Indeed, based on this $^{125}$IUDR assay, haptenization alone is more effective than irradiation at preventing proliferation. Accordingly, the tumor cell vaccine of the invention may be prepared by omitting the step of irradiation or any other treatment intended to prevent tumor cells from growing in the body of the patient upon injection; unexpectedly, hapteniziation alone is sufficient for that result.

The disclosures of each patent, patent application and publication cited or described in this document are hereby incorporated herein by reference, in their entirety.

Various modifications of the invention in addition to those shown and described herein will be apparent to those skilled in the art from the foregoing description. Such modifications are also intended to fall within the scope of the appended claims.

What is claimed is:

1. A method for inducing an anti-tumor response in a human patient suffering from a tumor, which method comprises administering to said patient a composition comprising a therapeutically effective amount of tumor cells that are:
   (i) conjugated to a hapten;
   (ii) of the same tumor type as the patient's tumor, and
   (iii) not allogeneic to said patient;
wherein hapten conjugation renders the tumor cells incapable of growing in the body of the patient, and wherein said tumor cells are not separately treated to render them incapable of growing in the body of the patient.

2. The method of claim 1 wherein said tumor cells are not irradiated.

3. The method of claim 1, wherein said administration is repeated at weekly intervals.

4. The method of claim 1, wherein said composition is administered for at least three times.

5. The method of claim 1, wherein said composition is administered for at least six times.

6. The method of claim 1 further comprising administering a therapeutically effective amount of cyclophosphamide prior to administration of said composition.

7. The method of claim 6, wherein cyclophosphamide is administered only prior to the first administration of said composition.

8. The method of claim 6 wherein said therapeutically effective amount of cyclophosphamide comprises administering a dose of about 300 mg/M$^2$ of cyclophosphamide.

9. The method of claim 1 wherein said tumor cells are selected from the group consisting of melanoma, lung, colon, breast, kidney, prostate, ovarian and leukemia tumor cells.

10. The method of claim 9, wherein said tumor cells are melanoma tumor cells.

11. The method of claim 1 wherein said hapten is selected from the group consisting of dinitrophenyl, trinitrophenyl, N-iodoacetyl-N'-(5-sulfonic-1-naphthyl)ethylene diamine, trinitrobenzenesulfonic acid, fluorescein isothiocyanate, arsenic acid benzene isothiocyanate, trinitrobenzenesulfonic acid, sulfanilic acid, arsanilic acid, dinitrobenzene-S-mustard and combinations thereof.

12. The method of claim 11 wherein said hapten is dinitrophenyl.

13. The method of claim 1 wherein said composition is administered with an adjuvant.

14. The method of claim 13 wherein said adjuvant is selected from the group consisting of Bacillus Calmette-Guerin, QS-21, detoxified endotoxin and a cytokine.

15. The method of claim 1 further comprising sensitizing the patient with a therapeutically effective amount of the hapten prior to administering said composition.

16. The method of claim 1 wherein said human is not sensitized to said hapten prior to administration of said composition.

17. The method of claim 1 wherein said composition comprises a maximum of about 7.5×10$^6$ tumor cells per dose.

18. The method of claim 1 wherein said anti-tumor response is at least one of the following: tumor necrosis, tumor regression, tumor inflammation, tumor infiltration by activated T lymphocytes, stable disease and prolongation of patient survival.

19. A composition for inducing an anti-tumor response in a human patient suffering from a tumor comprising a therapeutically effective amount of tumor cells that are:

(i) conjugated to a hapten;

(ii) of the same tumor type as the patient's tumor, and (iii) not allogeneic to said patient;

wherein hapten conjugation renders the tumor cells incapable of growing in the body of the patient, and wherein said tumor cells are not irradiated prior to administration to the patient.

20. The composition of claim 19 comprising a maximum of about 7.5×10$^6$ tumor cells.

21. The composition of claim 19 wherein said tumor cells are selected from the group consisting of melanoma, lung, colon, breast, kidney, prostate, ovarian and leukemia tumor cells.

22. The composition of claim 19 wherein said hapten is selected from the group consisting of dinitrophenyl, trinitrophenyl, N-iodoacetyl-N'-(5-sulfonic 1-naphthyl) ethylene diamine, trinitrobenzenesulfonic acid, fluorescein isothiocyanate, arsenic acid benzene isothiocyanate, trinitrobenzenesulfonic acid, sulfanilic acid, arsanilic acid, dinitrobenzene-S-mustard and combinations thereof.

23. The composition of claim 22 wherein said hapten is dinitrophenyl.

24. The composition of claim 19 further comprising an adjuvant.

25. The composition of claim 24 wherein said adjuvant is selected from the group consisting of Bacillus Calmette-Guerin, QS-21, detoxified endotoxin and a cytokine.

26. A method for rendering a human tumor cell incapable of growing, which method comprises the step of conjugating the human tumor cell to a hapten in vitro, wherein hapten conjugation renders said human tumor cell incapable of growing, and wherein said human tumor cell is not separately treated to render it incapable of growing.

27. The method of claim 26, wherein the human tumor cell is not irradiated.

28. The method of claim 26, wherein said human tumor cell is selected from the group consisting of a melanoma, lung, colon, breast, kidney, prostate, ovarian and leukemia tumor cell.

29. The method of claim 26, wherein said human tumor cell is a human melanoma cell.

30. The method of claim 26, wherein said hapten is selected from the group consisting of dinitrophenyl, trinitrophenyl, N-iodoacetyl-N'-(5-sulfonic 1-naphthyl) ethylene diamine, trinitrobenzenesulfonic acid, fluorescein isothiocyanate, arsenic acid benzene isothiocyanate, trinitrobenzenesulfonic acid, sulfanilic acid, arsanilic acid, dinitrobenzene-S-mustard and combinations thereof.

31. The method of claim 30, wherein said hapten is dinitrophenyl.

32. The method of claim 30, wherein said hapten is sulfanilic acid.

* * * * *